United States Patent [19]

Tavernarakis et al.

[11] Patent Number: 5,569,582
[45] Date of Patent: Oct. 29, 1996

[54] RAPID AMPLIFICATION AND DETECTION OF NUCLEIC ACIDS

[75] Inventors: Nectarios Tavernarakis; George Hatzidakis; Elias Krambovitis, all of Heraklion, Greece

[73] Assignee: Institute of Molecular Biology & Technology, Crete, Greece

[21] Appl. No.: 190,711

[22] Filed: Dec. 22, 1993

Related U.S. Application Data

[63] Continuation of Ser. No. 729,579, Jul. 15, 1991, abandoned.
[51] Int. Cl.$^6$ .............................. C12Q 1/70; C12Q 1/68; C07H 21/04
[52] U.S. Cl. .............................. 435/5; 435/6; 536/24.33; 536/24.3; 536/24.32; 935/77; 935/78
[58] Field of Search .......................... 435/5, 6, 91.2; 536/24.32, 24.33, 24.32, 24.33

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,752,566 | 6/1988 | Collins et al. | 435/6 |
| 4,766,062 | 8/1988 | Diamond et al. | 435/6 |
| 4,766,064 | 8/1988 | Williams et al. | 435/6 |
| 4,767,699 | 8/1988 | Vary et al. | 435/6 |
| 4,800,159 | 1/1989 | Mullis et al. | 435/172.3 |
| 4,888,278 | 12/1989 | Singer et al. | 435/6 |
| 4,889,818 | 12/1989 | Gelfand et al. | 435/194 |
| 4,895,955 | 1/1990 | Ford et al. | 548/303 |
| 4,902,624 | 2/1990 | Columbus et al. | 435/316 |

FOREIGN PATENT DOCUMENTS

| | | |
|---|---|---|
| 0297379 | 4/1989 | European Pat. Off. . |
| 0371437 | 6/1990 | European Pat. Off. . |

OTHER PUBLICATIONS

Kim, H.-S., and O. Smithies, Recombinant fragment assay for gene targetting based on the polymerase chain reaction, Nucleic Acids Res. (1988) 16:8887–8903.

Ratner, L., et al. Complete nucleotide sequence of the AIDS virus, HTLV–III., Nature (Jan. 24, 1985) 313:277–284.

Sheffield, V. C., et al. Attachment of a 40–base–pair G&C–rich sequence (GC–clamp) to genomic DNA fragments . . . , Proc. Natl. Acad. Sci. USA (Jan., 1989) 86:232–236.

Gyllensten, V. B., and H. A., Erlich, Generation of single–stranded DNA by the polymerase chain reaction and its application . . . , Proc. Natl. Acad. Sci. USA (Oct, 1988) 85:7652–7656.

Nagata, Y., et al. Quantification of picogram levels of specific DNA immobilized in microfilter wells, FEBS Letters (Apr., 1985) 183:379–382.

Verbeek, A., and P. Tijssen, Polymerase chain reaction for probe synthesis and for direct amplification . . . , J. Virol. Methods, (1990) 29:243–256.

Carman, W. F., and A. H. Kidd, An assessment of optimal conditions for amplification of HIV cDNA using *Thermus aquaticus* polymerase, J. Virol. Methods (1989) 23:277–290.

Carman, W. F., et al., Reverse transcription and subsequent DNA amplification of rubella virsu RNA, J. Virol. Methods (1989) 25:21–30.

Sadaie, M. R., et al., Site–directed mutagenesis of two trans–regulating genes (*tat*–III, *trs*) of HIV–I, Science (Feb. 19, 1988) 239:910–913.

Laure et al., "Detection of HIV DNA in Infants and Children by Means of the Polymerase Chain Reaction," *The Lancet*, Sep. 3, 1988, pp. 538–540.

Williams, "Optimization Strategies for the Polymerase Chain Reaction," *BioTechniques*, 7:762–768 (1989).

"The Hackers Guide to PCR," *Polymerase Chain Letter*, 1:1–13 (1989).

Gibbs, et al., "The Polymerase Chain Reaction: a Meeting Report," *Genes & Development*, 3:1095–1098.

Syvanen et al., "Quantification of Polymerase Chain Reaction Products by Affinity–Based Hybrid Colection," *Nucleic Acids Res.*, 16:11327–11338 (1988).

Lee et al., "High Rate of HTLV–II Infection in Seropositive IV Drug Abusers in New Orleans," *Science*, 244:471–475 (1989).

Keller et al., "Section 6: Probe and Target Amplification Systems," *DNA Probes*, (Stockton Press 1989) pp. 215–223.

Hart et al., "Direct Detection of HIV RNA Expression in Seropositive Subjects," *The Lancet*, Sep. 10, 1988, pp. 596–599.

*Primary Examiner*—Stephanie W. Zitomer
*Assistant Examiner*—Lisa Arthur
*Attorney, Agent, or Firm*—Dickstein Shapiro Morin & Oshinsky LLP

[57] ABSTRACT

Disclosed herein are methods, primers, probes, and kits for the rapid amplification and detection of nucleic acids. The invention provides improved methods for amplifying small amounts of nucleic acid in a sample in which the amplification steps are conducted at the same temperature, or alternatively, at two different temperatures. The invention also provides improved methods for detecting the amplified nucleic acid in which the detection signal is boosted. Related probes and test kits are also provided. The invention is particularly useful in the detection of HIV-1.

18 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 19 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

GAAGGAGCCA CCCCACAAG                                                      19

( 2 ) INFORMATION FOR SEQ ID NO:2:

( i ) SEQUENCE CHARACTERISTICS:
        ( A ) LENGTH: 19 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GGCTGCTTGA TGTCCCCCC                                                      19

( 2 ) INFORMATION FOR SEQ ID NO:3:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TTTAAACACC ATGCTAAACA CAGT                                                24

( 2 ) INFORMATION FOR SEQ ID NO:4:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GACATCGAGC TTGCTAGAAG                                                     20

( 2 ) INFORMATION FOR SEQ ID NO:5:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

TATTGAGGCT TAAGCAGTGG        20

( 2 ) INFORMATION FOR SEQ ID NO:6:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

CTCTCTTTAA ACACCATGCT AACACAGT        28

RAPID AMPLIFICATION AND DETECTION OF NUCLEIC ACIDS

This application is a continuation of application Ser. No. 07/729,579, filed Jul. 15, 1991, now abandoned.

FIELD OF THE INVENTION

This invention relates to the rapid amplification and detection of nucleic acids. In particular, the invention provides improved methods for amplifying small amounts of nucleic acids in a sample in which the amplification steps are conducted at the same temperature or, alternatively, at only two different temperatures. In addition, the invention provides improved methods for detecting the amplified nucleic acids in which the detection signal is boosted. Related probes and test kits are also provided. The invention is expected to be useful in a wide variety of fields, including scientific, clinical, and forensic analysis. In one specific embodiment, it is particularly useful in the detection of human immunodeficiency virus type 1 (HIV-1), the causative agent of AIDS.

BACKGROUND OF THE INVENTION

The ability to detect exceedingly small amounts of a nucleic acid in a sample generally requires the amplification of the amount of the target nucleic acid. This is especially important for the detection of human retroviruses, where positive samples may contain only 5–10 target molecules in $10^6$ cells.

The preferred method for amplifying target DNA has been the polymerase chain reaction (PCR) technique. The technique has been described in U.S. Pat. No. 4,683,195, issued Jul. 28, 1987 to Mullis, et al., U.S. Pat. No. 4,683,202, issued Jul. 28, 1987 to Mullis, U.S. Pat. No. 4,800,159, issued Jan. 24, 1989 to Mullis, et al., U.S. Pat. No. 4,889,818, issued Dec. 26, 1989 to Gelfand, et al., and U.S. Pat. No. 4,902,624, issued Feb. 20, 1990 to Columbus, et al., all of which are incorporated herein by reference.

In general, the PCR reaction involves the use of a pair of specific oligonucleotide primers to initiate DNA synthesis on a target DNA template. Two oligonucleotide primers are used for each double-stranded sequence to be amplified. The target sequence is denatured into its complementary strands. Each of the primers, which are sufficiently complementary to a portion of each strand of the target sequence to hybridize with it, anneals to one of the strands. The primers are extended, using nucleosides in the sample and a polymerization agent, such as heat-stable Taq DNA polymerase. This results in the formation of complementary primer extension products, which are hybridized to the complementary strands of the target sequence. The primer extension products are then separated from the template strands, and the process is repeated until the desired level of amplification is obtained. In subsequent cycles, the primer extension products serve as new templates for synthesizing the desired nucleic acid sequence.

By repeating the cycles of denaturation, annealing, and extension, the original target DNA can be amplified exponentially according to the formula $2^n$, where n is the number of cycles. In theory, 25 cycles, for example, would result in a $3.4 \times 10^7$-fold amplification. However, since the efficiency of each cycle is less than 100%, the actual amplification after 25 cycles is about $1-3 \times 10^6$-fold. The size of the amplified region is generally about 100–400 base pairs, although stretches of up to 2 kb can be amplified. See Keller and Manak, *DNA probes* (New York: Stockton Press, 1989), pgs. 215–216.

The three basic steps of the PCR reaction—denaturation, annealing, and extension—are driven and controlled by the temperature of the reaction mixture, with each step occurring at a different temperature. Somewhat different temperature ranges are disclosed for each of the three steps in the above-referenced patents. However, as time passed, those skilled in the art have settled on fairly standard temperatures for each of the steps in the cycle. Thus, Gelfand, et al., discloses a denaturing temperature range of about 90°–105° C., preferably 90°–100° C., an annealing temperature range of about 35°–65° C., preferably 37°–60° C., and an extension temperature range of about 40°–80° C., preferably 50°–75° C. For Taq polymerase, which is the overwhelmingly preferred polymerase for the PCR reaction, Gelfand, et al., refers to an annealing temperature range of about 45°–58° C. and an extension temperature range of about 65°–75° C. Columbus, et al., which is directed to a temperature cycling cuvette for use in PCR, refers to temperature ranges of 92°–95° C. for the denaturing step, 50°–60° C. for the annealing step, 70° C. for the extension step. Keller and Manak, cited above, refer to a denaturation temperature of about 93° C., an annealing temperature of 37°–55° C., and a primer extension temperature of 70° C.

The PCR technique has been modified to permit the amplification of viral RNA. See Murakawa, et al., DNA, 7:287–295 (1988), which is incorporated herein by reference. The article discloses the amplification of sequences from HIV-1 RNA templates for the identification of HIV-1 in peripheral blood and tissue samples obtained from AIDS and ARC patients. Total nucleic acid is isolated from infected cells, and the DNA is digested with RNase-free DNase so that it does not contribute to the final PCR product. A cDNA copy of a target sequence of the viral RNA is synthesized, using the PCR primers and reverse transcriptase. The one primer complementary to the RNA serves to initiate cDNA synthesis.

Several different formats have been used for the detection of PCR products. Generally, a radioactive or nonradioactive labeled probe that is complementary to the target sequence is used. The hybridization of the probes to the amplified target sequence, and the subsequent detection of the labeled moiety results in the detection of the target sequence. Nonradioactive labeled probes are generally more desirable because they obviate the need for special handling procedures. However, they may not generate as intense a signal, or the signal may be obscured by background "noise." Thus, there is a need for enhancing the intensity of the signal in such probes.

The PCR technique is a revolutionary one, and it is widely used. Nevertheless, it does have significant drawbacks. The most serious of these is nonspecific hybridization, which results in false positives. Avoiding nonspecific hybridization requires ultrapure reagents. Unfortunately, for most clinical and diagnostic applications, it is desirable to use "dirty" samples, which presents a major problem, unless time-consuming and expensive sample preparation is undertaken.

Another important drawback to the PCR technique is the time involved in amplification. Although the usual six hour time period for PCR is far superior to an alternative technique such as cloning, which can take days or weeks, it would still be desirable to cut amplification time by one-half to two-thirds.

The present invention overcomes these drawbacks of the PCR technique, and it provides an improved detection system. The invention provides methods for the rapid amplification and detection of nucleic acids in which the denaturing, annealing, and extension steps occur all at the same temperature or, alternatively, at only two different temperatures, thus providing for faster cycling. In addition, the invention provides amplification methods where the annealing temperature is higher than the prior art temperatures, thus eliminating nonspecific hybridization. Finally, the invention provides improved methods of detecting the amplified nucleic acids through a two-stage signal amplification.

SUMMARY OF THE INVENTION

It is an object of the present invention to provide methods for amplifying a target nucleic acid sequence in a sample.

Another object is to provide methods for detecting or measuring the presence of a target nucleic acid sequence in a sample.

Still another object of the invention is to provide a kit for detecting or measuring the presence of a target nucleic acid sequence in a sample.

A further object of the invention is to provide primer pairs for use in amplifying a nucleic acid sequence of HIV-1 DNA.

A still further object is to provide a probe for use in detecting a nucleotide sequence complementary to a target nucleic acid sequence of HIV-1 DNA.

Additional objects and advantages of the invention will be set forth in part in the description that follows, and in part will be obvious from the description, or may be learned by the practice of the invention. The objects and advantages of the invention will be attained by means of the instrumentalities and combinations particulary pointed out in the appended claims.

To achieve the objects and in accordance with the purpose of the invention, as embodied and broadly described herein, the present invention provides a method for amplifying a target nucleic acid sequence in a sample. The sequence is part of a nucleic acid, which the sample is suspected of containing. Preferably, the target nucleic acid is DNA, most preferably HIV-1 DNA.

Nucleoside triphosphates, primer pairs consisting of two oligonucleotide primers, and a nucleic acid polymerase are added to the sample. Each primer is an oligonucleotide having a region that is complementary to and hybridizes with a different strand of the target sequence. It is effective as an initiator for nucleoside polymerization. If double stranded, the nucleic acid in the sample is denatured so that separate strands of the target nucleic acid sequence are formed. Preferably, the denaturing is accomplished by heating the sample to about 95° C.

A reaction temperature in a range from about 68° C. to about 80° C. (preferably about 75° C.) and appropriate reaction conditions are maintained so that the following cycle occurs. First, the primers anneal (hybridize) to the separate strands of the target sequence. The primers and the nucleic acid polymerase initiate the synthesis of primer extension products, formed by the nucleosides attaching to the primer and forming a polymer, using the target sequence strand as a template. Thus, the primer extension products are annealed or hybridized to the strands. The primer extension products are then separated from the strands to become templates for the primers, and the cycle is repeated, with new primer extension products being formed. The reaction is allowed to continue for a sufficient number of cycles until the desired amplification of the target nucleic acid sequence has been accomplished. The primers are chosen so that they bind strongly to the strands of the target sequence, but the extension from each primer binds weakly to the strand.

In an alternative embodiment of the invention, the cycling occurs at two different temperatures. The reaction temperature is maintained in a range from about 68° C. to about 82° C. (preferably about 70° C.) and appropriate reaction conditions are maintained to form the primer extension products. These are separated from the strands by raising the temperature to a range of about 88° C. to about 96° C. (preferably about 90° C.) to produce single-stranded molecules. The temperature is then lowered back to the previously mentioned range, permitting the primers to anneal to the single-stranded molecules and primer extension products to be synthesized, using the single-stranded molecules as templates. The temperature cycling is repeated a sufficient number of times to obtain the desired amplification of the target nucleic acid sequence.

The invention also provides methods for detecting or measuring a target nucleic acid sequence in a sample, based upon the amplification methods discussed above. In these methods, some of the nucleoside triphosphates are biotin-labeled. This produces nucleotide sequences that are copies of the target sequence which contain one or more biotin-labeled nucleotides. Such sequences are rendered single-stranded and contacted with immobilized probes. Each of the probes is a single-stranded polynucleotide attached to a solid support and capable of hybridizing with one of the single-stranded nucleotide sequences. The probes are contacted with the sample for a sufficient time and under appropriate hybridizing conditions to permit the polynucleotides to hybridize with the single-stranded nucleotide sequences. This forms bound complexes comprised of both of these entities. The presence of the biotin in the bound complexes is then detected or measured. Preferably, the biotin is detected by contacting the bound complexes with a detectable moiety that binds to biotin, such as avidin-horseradish peroxidase, and then detecting the detectable moiety, i.e., the horseradish peroxidase.

In an alternative and prefered embodiment, the detecting step is accomplished by contacting the bound complexes with a first moiety that binds to biotin, such as avidin. A second moiety, comprising biotin bound to detectable moiety, such as horseradish peroxidase, is then added. The biotin in this second moiety binds to the first moiety. The detectable moiety is then detected. This provides a two-stage amplification of the signal.

The invention further provides kits for detecting or measuring the presence of a target nucleic acid sequence in a sample. The kits contain biotin-labeled nucleoside triphosphates and a primer pair specific for the particular target sequence sought to be detected or measured. Preferably, the kit further comprises a probe that is specific for the target sequence. It may also contain a nucleic acid polymerase, reagents for detecting or measuring the biotin, denaturing reagents, and/or controls.

In a preferred embodiment of the kit, the target nucleic acid sequence is HIV-1 DNA. The primer pair comprises the nucleotide sequences

| 5' GAAGGAGCCA CCCCACAAG 3' | (SEQ ID NO: 1) |
| 3' CCCCCCTGTA GTTCGTCGG 5' | (SEQ ID NO: 2) | and the probe comprises the nucleotide sequence

| 5' TTTAAACACC ATGCTAAACA CAGT 3'. | (SEQ ID NO: 3) |
|---|---|

DETAILED DESCRIPTION OF THE INVENTION

Reference will now made in detail to the presently preferred embodiments of the invention which, together with the following examples, serve to explain the principles of the invention.

The invention provides improved methods for amplifying and detecting nucleic acids. The target nucleic acid may be single or double-stranded DNA or RNA from any organism. Such organisms include plants, animals, and microorganisms, such viruses, viroids, mycoplasma, bacteria, and fungi. The viruses include DNA and RNA viruses. In a preferred embodiment, the viruses are retroviruses, and in a particularly preferred embodiment, they are the AIDS-related viruses (including HIV-1 and HIV- 2). The term "animals" includes mammals, and, in a preferred embodiment, the target nucleic acid is mammalian nucleic acid, such as mitochondrial or genomic DNA or the various types of RNA. Such nucleic acid further includes human cellular oncogene sequences and human structural gene sequences.

The sample may be anything that contains nucleic acid, obtained from a source by techniques known to those skilled in the art. It may be further processed by known techniques, such as being subjected to extraction procedures, to render it in a form usable in the method of the invention. For example, the method of the present invention can be applied to determine if a patient has been infected by a virus. A sample of body fluid or tissue that contains the virus is obtained from the patient. In this case, the sample should contain cells that are capable of being infected by the virus or should contain body fluid in which the virus or viral nucleic acid is known to accumulate. The viral nucleic acid is extracted from the sample by known techniques.

A target nucleotide sequence within the target nucleic acid is selected so as to provide a target of sufficient specificity and uniqueness in order to be identified and distinguished from other nucleic acid molecules in the sample. Among other things, it will be selected on the basis of a nucleotide base sequence specific to the organism. For many viruses, in particular those that mutate at high rates, it is advisable to select a target sequence from a well-conserved region of the viral genome.

The target nucleotide sequence may consist of from about 50 to about 4000 base pairs, but preferably consists of about 55 to about 200 base pairs, and most preferably consists of about 60 to about 100 base pairs. In the case of HIV-1 DNA, the preferred target sequences are the nucleotide sequence 1317–1379 of pHXB2 and 331–530 of pHXB2, depending upon which primer pair of the invention is used to amplify the sequence.

In the preferred embodiment of the invention, the target sequence is amplified in a reaction that occurs at a single temperature, after the initial denaturation of the nucleic acid, in contrast to the three different temperatures in the PCR technique. We call this method the Continuous Enzyme Reaction (CER). In the first step, certain reagents are added to the sample that contains the target nucleic acid. In particular, nucleoside triphosphates, including biotinylated nucleotide triphosphates, primer pairs, and a nucleic acid polymerase are added. Preferably, they are added as part of a buffered solution. Each primer is an oligonucleotide having a region that is complementary to and hybridizes with a different strand of the target sequence. It is effective as an initiator for nucleoside polymerization. Preferably, the length of each primer is approximately 15–25 nucleotides.

The target nucleic sequence, if it is double-stranded, is then separated into single strands by known techniques. Preferably, the nucleic acid is denatured by heating the sample to about 95° C. The target sequence may be denatured before the other reagents are added to the sample, although it is preferable to denature it afterwards.

The sample is then maintained under appropriate reaction conditions to permit the following cycle to occur: (1) each of the oligonucleotide primers anneals (hybridizes) to each of the strands of the denatured target sequence; (2) primer extension products are synthesized from the nucleoside triphosphates, with the synthesis being initiated by the primer and catalyzed by the nucleic acid polymerase; and (3) a portion of the extension products, which are hybridized to the strands of the target sequence, separate spontaneously from the strands. The separated extension products become templates for the primers, and the cycle is repeated. Such reaction conditions include maintaining the reaction temperature somewhere in the range from about 68° C. to about 80° C. Preferably, the temperature is maintained at about 75° C.

The reaction is permitted to proceed for a sufficient period of time so that the cycle is repeated about 10 to about 25 times. This will occur over a time ranging from about 1.0 hours to about 2.5 hours. Generally, the longer reaction time is preferred.

The nucleoside triphosphates are readily available commercially or can be synthesized by those skilled in the art. When the method of the invention is applied to the amplification of DNA, deoxyribonucleoside triphosphates are used.

Most preferably, some of the nucleoside triphosphates or deoxyribonucleoside triphosphates are labeled with biotin. This permits the incorporation of a reporter molecule into the amplified sequences, which can be detected by the means described below. Such biotin-labeled nucleoside triphosphates can be synthesized by known techniques or are commercially available. The preferred biotin-labeled nucleoside triphosphate is Bio-dUTP. The labeled nucleosides are used in a concentration of about 10 uM to about 5 mM, and preferably from about 0.1 mM to about 0.5 mM.

The polymerizing agent is any polymerase for nucleic acid. Preferably, it is Taq polymerase, which is heat stable under these reaction conditions.

The primer pairs consist of two oligonucleotide primers. Each primer is an oligonucleotide having a region that is complementary to and hybridizes with a different strand of the target sequence, and is effective as an initiator (primer) for nucleoside polymerization. The primers of the invention are selected so as to meet two requirements. First, they must bind strongly to the strands of the target sequence to allow binding at a temperature higher than the temperature preferred in the literature. Second, the product from the extension of the primers, which is synthesized from the nucleosides in the presence of the polymerase, is the least stable of a series of products which were initially selected and more likely to dissociate spontaneously to single-stranded form, thus itself becoming a target sequence of the appropriate primer. As used herein, the term "bind strongly" and variations thereof means adequately stable single-stranded DNA-primer hybrids are formed at the high temperature of the invention.

This is accomplished by choosing primers where the ratio of G and C to A and T in the primers ranges from about 1.5:1 to about 3.0:1. Preferably, the ratio is about 3.0:1. This is confirmed by the temperature of dissociation (Td) of the primer pair and the melting temperature (Tm) of the extension products. The Td of the primer pair is calculated from the formula Td=4° (C+G)+2° (A+T). The Tm, which is the temperature at which the extension products are denatured, is calculated from the formula:

$$Tm=81.5°+16.6 \log Ci+0.41 \text{ (\% C+G)}-0.72 \text{ (\% formamide)}-82°/n-1.5 \text{ (\% mismatch)}$$

where $Ci$ is the ionic strength of the reaction solution and n is the number of nucleotides.

For HIV-1 DNA, the following specific primers, which we call HOPE 1 and HOPE 2, are preferred:

| HOPE 1: | 5' GAAGGAGCCA CCCCACAAG 3' | (SEQ ID NO: 1) |
|---------|----------------------------|----------------|
| HOPE 2: | 3' CCCCCCTGTA GTTCGTCGG 5' | (SEQ ID NO: 2) |

These primers produce HIV-1 DNA sequences in positions 1317–1379 of the plasmid pHXB2, which are 63 base pairs long. The Td for HOPE 1 is 62° C. and that for HOPE 2 is 64° C. The Tm of the product, i.e., the primer extension, is 76.7° C.

The use of primers meeting the above-stated conditions permits the maintenance of temperature and other reaction conditions whereby the amplification cycle occurs at a single temperature rather than three different temperatures. In order for the reaction to occur efficiently in terms of yielding double-stranded target DNA, the following reaction conditions should be considered:

1) The temperature should be high enough so that a substantial portion of the target DNA is found in single-stranded form, available for primer hybridization (the activity of the polymerase is a limiting factor).

2) The concentration of the primers should be high enough so as to favor single-stranded DNA-primer hybrid formation.

3) The GC content of the primers should be such as to allow an adequately stable single-stranded DNA-primer hybrid to be formed at the high temperature chosen.

4) The primer extension product, on the contrary, should be as unstable as possible so that the probability for the two strands to dissociate spontaneously is as high as possible.

5) The polymerizing agent should be able to efficiently polymerize dNTPs at the high temperature chosen and also to incorporate the dNTP analogue used as a label onto DNA strands.

Generally, the cycle of primer annealing, primer extension, and extension product denaturing occurs from about 10 to about 25 times. The time period for this to occur is approximately 0.5 hours to overnight.

In an alternative and preferred embodiment, asymmetric concentrations of the primers are used. That is, the concentration of one of the primers exceeds that of the other by a factor of about $10^3$ to 1, and preferably by about $10^2$ to about 1. This permits the build up of only one instead of two primer extension products. Therefore, there is only a limited risk of DNA-DNA complexing during hybridization. Instead, the product DNA will bind to the primer or the probe that is used for detection of the amplified DNA. This enhances both the specificity and sensitivity of the assay.

When the nucleic acid to be amplified is RNA, certain modifications are made. The RNA template in infected cells is either viral mRNA or packaged virion RNA. Total nucleic acid is isolated in crude form by known methods, or it can be purified by, for example, phenol-chloroform extraction. Residual DNA may be digested with RNase-free DNase so that it does not contribute to the amplified sequences. A cDNA copy of a target ribonucleotide sequence in the target RNA is synthesized, using the primers and reverse transcriptase. The primer complementary to the target sequence serves to initiate cDNA synthesis. The single-stranded cDNA product can be amplified after heat inactivation of the reverse transcriptase and adjustment of the reaction conditions to those of the method of the invention.

In an alternative embodiment of the invention, the amplification of the target nucleic acid sequence occurs at two different temperatures. The primer annealing and extension steps occur at one temperature, and the denaturing of the primer extension products occurs at another temperature. We call this method the Accelerated Chain Enzyme Reaction (ACER).

In particular, the reaction temperature is maintained at a point in the range from about 68° C. to about 82° C. for primer annealing and extension. Preferably, the reaction temperature for these steps of the cycle is about 70° C. The primer extension products are separated from the target sequence strands or other extension products by raising the temperature to a range of about 88° C. to about 96° C. This denatures the extension products from the template, producing single-stranded molecules that serve as further templates when the temperature is lowered. Preferably, the denaturing step occurs at a temperature of about 90° C.

The cycling between these two temperatures is repeated about 10 to about 25 times. The reaction time for these steps is from about 0.5 hours to about 3 hours. Generally, the time is about 1.5 hours.

The preparation of the sample and the initial reaction mixture is essentially the same as in the single temperature method. The target nucleic acid sequence is also denatured in the same manner. This method also lends itself to the use of asymmetric concentrations of primers and to the amplification of RNA as discussed previously.

The specific primers for any given target sequence are determined as discussed above with respect to the single temperature embodiment. The primers will have the same general characteristics mentioned above. For HIV-1 DNA, the previously mentioned HOPE 1 and HOPE 2 primers are preferred. In addition, two other primers, which we designate NIDA 1 and NIDA 2, are preferred. These primers comprise the following sequences:

| NIDA 1: | 5' GACATCGAGC TTGCTAGAAG 3' | (SEQ ID NO: 4) |
|---------|-----------------------------|----------------|
| NIDA 2: | 3' GGTGACGAAT TCGGAGTTAT 5' | (SEQ ID NO: 5) |

They produce HIV-1 DNA sequences in positions 331–530 pHXB$_2$.

In another embodiment, the invention comprises a method for detecting or measuring a target nucleic acid in a sample. The target sequence is amplified according to the methods discussed above, wherein some of the nucleoside triphosphates are biotin-labeled. This produces nucleotide sequences that are copies of the target sequence and contain one or more biotin-labeled nucleotides. The amplified sequences, which will be double-stranded, are then rendered single-stranded by known techniques, preferably heat denaturation at a temperature of about 88° C. to about 96° C. The sample is then contacted with immobilized probes. These probes are single-stranded polynucleotides attached to a solid support. Each one is capable of hybridizing with one of the single-stranded nucleotide sequences. The probes are contacted with the sample for a sufficient time and under appropriate hybridizing conditions known to those skilled in the art to permit the polynucleotides to hybridize with the single-stranded nucleotide sequences. This forms bound complexes of the polynucleotides and the single-stranded nucleotide sequences.

The probes can be prepared by standard techniques known to those skilled in the art, given the particular target sequence and the teachings contained herein. When the nucleic acid is HIV-1 DNA, the preferred probe comprises the sequence 5' TTTAAACACC ATGCTAAACA CAGT 3' (SEQ ID NO: 3), which we call the HOPE 3 probe. The HOPE 3 probe may also be used with a pyrimidine spacer at the 5' end. Preferably, the spacer is CTCTC, in which case we call the probe HOPE 4.

The solid support may be any solid material to which the probe may be attached. Such material includes filters, resins, beads, cubes, and microtiter plates. Preferably, the solid supports are the wells in plastic microtiter plates, such as polystyrene microtiter plates. Most preferably, the probe is first chemically coupled to a protein carrier, such as bovine serum albumin, which is then immobilized onto polystyrene microtiter plate wells. See Running and Urdea, *BioTechniques*, 8:276–277 (1990) and Nagata, et al., *FEBS Letters*, 183:379–382 (1985), both of which are incorporated herein by reference.

The single-stranded polynucleotide of the probe is attached to the solid support covalently or noncovalently by means known to those skilled in the art. Preferably, the probe is chemically coupled to a protein, such as bovine serum albumin, or other carrier, such as polyethylene glycol. A spacer between the carrier and the probe may also be used. The polynucleotide comprising the probe may contain from about 15 to about 2,000 nucleotides. Preferably, it contains from about 15 to about 200 nucleotides and most preferably from about 15 to about 40 nucleotides.

The final step in this method of the invention is to detect or measure the presence of biotin in the bound complex. One way of doing so is to contact the bound complexes with a detectable moiety that binds to the biotin and then to detect such moiety. Preferably, such detectable moiety is comprised of a molecule or compound that binds to the biotin, such as avidin or streptavidin, coupled to a detectable entity (e.g., a detectable molecule or compound), such as horseradish peroxidase. The horseradish peroxidase is detected by known means. Other detectable moieties/detectable entities are disclosed in U.S. Pat. No. 4,711,955 issued Dec. 8, 1987 to Ward et al., which is incorporated herein by reference.

Preferably, the bound complexes are washed with a liquid, such as a buffer solution, before and/or after contact with the detectable moiety to remove any unbound, labeled sequences or labeled nucleoside triphosphates that may be present.

In a particular preferred embodiment, the invention provides a method for a two-stage amplification of the signal provided by the biotin. The method may be used to detect target nucleic acid sequences that have been amplified through the formation of primer extension products that contain one or more biotin-labeled nucleotides. Thus, it is particularly applicable to the amplification methods of the present invention, but it is not limited to them.

Such amplified sequences are rendered single-stranded, and the sample containing such single-stranded sequences is contacted with immobilized probes as discussed above. The bound complexes comprising the single-stranded sequences and the single-stranded polynucleotides of the probes are then contacted with a first moiety that binds to biotin. The moiety is preferably avidin or streptavidin. A second moiety, comprising biotin bound to a detectable moiety, is then added to the sample. The biotin in the second moiety binds to the first moiety, which is bound to the biotin in the amplified sequences. The detectable moiety is then detected or measured by standard techniques. Preferably, such detectable moiety is horseradish peroxidase. Preferably, the solid support is washed between the steps discussed above in order to remove unbound materials that may interfere with the detection procedure or give a false signal.

The present invention also comprises a kit for detecting or measuring the presence of a target nucleic acid sequence in a sample suspected of containing that sequence. The kit comprises biotin-labeled nucleoside triphosphates and an appropriate primer pair. Each primer comprises an oligonucleotide having a region that is complementary to and hybridizes with a different strand of the target sequence and is effective as a primer for nucleoside polymerization. Preferably, the kit further comprises a probe that is complementary to and hybridizes with the target sequence. Most preferably, the kit further comprises a nucleic acid polymerase, preferably Taq polymerase, and additional means, such as reagents, for detecting or measuring the biotin, denaturing double-stranded polynucleotides, and providing a control against which the results may be evaluated.

In a particularly preferred embodiment, the invention provides a kit for detecting or measuring the presence of a target nucleic acid sequence in HIV-1 DNA in a sample. The kit contains biotin-labeled nucleoside triphosphates, unlabeled nucleoside triphosphates, a primer pair comprising the nucleotide sequences:

| 5' GAAGGAGCCA CCCCACAAG 3' | (SEQ ID NO: 1) |
| 3' CCCCCCTGTA GTTCGTCGG 5' | (SEQ ID NO: 2) | and a probe comprising the nucleotide sequence

| 5' TTTAAACACC ATGCTAAACA CAGT 3'. | (SEQ ID NO: 3) |

It is to be understood that the application of the teachings of the present invention to a specific problem or environment will be within the capabilities of one having ordinary skill in the art in light of the teachings contained herein. Examples of the products and processes of the present invention appear in the following examples.

EXAMPLE 1

Isolation of DNA From Blood

For AIDS screening, the object is a rapid and safe extraction of DNA to allow the processing of many samples. The suggested method is the following. Four hundred microliters (400 ul) of blood is collected in a tube containing anti-clotting agent (citrate or EDTA) and is contrifuged (e.g. 3,000 g for 5 minutes or 10,000 g for 5–10 seconds). The upper buffy-coat layer is removed, or the whole pellet is suspended in 200 ul distilled water in order to lyse the cells. The lysed cell suspension is boiled at 100° C. in order to break up the cell nuclei. Centrifugation for 5 minutes at 10,000 g removes insoluble debris. The resultant supernatant is used for subsequent manipulations.

EXAMPLE 2

One Temperature Reaction (CER)

Fifteen ul of DNA sample prepared as in Example 1 are added to 80 ul of a reaction buffer. The reaction buffer contains 0.3 nmol of each primer (HOPE 1, HOPE 2), 10 mM Tris-HCl, pH 8.4 (20° C.), 50 mM KCl, 2 mM $MgCl_2$, 0.1% gelatin. 0.5 mM dATP, dCTP, dGTP, 150 uM dTTP, 350 uM Bio- 11-dUTP, and 0.1% BSA (nuclease free). The reaction mix is incubated at 95° C. for five minutes. This is to initially denature the DNA. The mix is then allowed to cool down to room temperature, three units of the enzyme VENT™ Polymerase (New England Biolabs) are added, and mineral oil is layered at the top. The reaction then takes place at 78° C. for 3–4 hours.

EXAMPLE 3

Two Temperature Reaction (ACER)

Ten microliters of the DNA containing supernatant prepared as in Example 1 are used for this amplification reaction. This volume is mixed with 90 ul of reaction buffer. The reaction buffer comprises 100 pmol of each primer (melting temperature higher than 62° C., i.e., NIDA1, NIDA2), 10 mM Tris-HCl, pH 8.0 (20° C.), 1.8 mM $MgCl_2$, 50 mM KCl, 0.05% gelatin, 0.1 mM dATP, dCTP, dGTP, 03 nM dTTP, 70 nM Bio-11-dUTP, and 0.1% BSA (nuclease free).

The reaction mixture is then layered with one or two drops of any mineral oil and transferred to a programmable heat block where amplification takes place. The temperatures used are 90° C. for the initial and subsequent denaturation steps, and 70° C. for annealing and elongation. The incubation period allowed for denaturation is one minute and for annealing, which is coupled with elongation, two minutes. This thermal profile is repeated 20 times, with the annealing-elongation step of the 20th cycle being the last step of the reaction. Reaction products are stored at 4° C. for further manipulation. The amplification reaction takes place in the wells of a 96-well ELISA plate, a very convenient way when dealing with a large number of samples.

EXAMPLE 4

Two Temperature Asymmetric Reaction (AACER)

This type of reaction is essentially the same as the ACER, except for the amount of the primers, which now is 20 pmol for HOPE 1 and 300 pmol for HOPE 2. The volume of the DNA sample is also increased to 20 ul.

EXAMPLE 5

Detection of Amplified Products

The totality (100 ul) of the amplification reaction volume (ACER or CER) is applied to a well containing immobilized probe after heat denaturation (100° C., five minutes) and snap cooling on ice. (Denaturation is not necessary when asymetric two temperature, or one temperature reactions are performed.) Hybridization is allowed to proceed for one hour at 37° C. Unbound material is removed by washing four times with 0.9M NaCl.

A 50 ng/ml solution of avidin-HRP in 10mM Tris-HCl pH 7.4 (20° C.), 5% gelatin, and 2% BSA is added to the well. After incubating 30 minutes at room temperature with shaking, the well is washed with 0.9M NaCl, 10mM Tris-HCl, pH 7.4 (20° C.), and 0.1% Tween-20. The substrate mix is then applied (0.05% TetraMethylBenzidine, 10% $H_2O_2$). Blue color develops within 10 minutes. The colorigenic reaction is stopped with 0.5% $H_2SO_4$, and absorbance at 450 nm is measured.

EXAMPLE 6

Preparation of the Primers

The synthesis of the primers is standard and automated (Applied Biosystems synthesizer, model 380B). Synthesis is based on a solid phase chemistry where the first base is already bound to a controlled pore glass (CPG) support at the 3' end. The 5' end is protected with a dimethoxytrityl group. Each new base is covalently coupled to the previous base at the 5' end using a complete synthesis cycle. The cycle consists of 4 steps:

1. Detritylation. The attached (terminal) base is detritylated with trichloroacetic acid creating a free hydroxyl group.

2. Activation and addition. The next base is activated with tetrazole at the 3' end and then is passed through the CPG column allowing it to react with 5' hydroxyl of the terminal base.

3. Capping. The unreacted 5' hydroxyl groups (approximately 0–2%) are blocked with acetic anhydride (acetylation).

4. Oxidation. The phosphorous of the new base is oxidized from the trivalent to the pentavalent form using a iodine-water-lutidine-tetrahydofuran mixture.

After the completion of the synthesis cycle, the new base is accessible for the repeat of the cycle with the next base. Thus, elongation of the DNA chain is achieved with the correct nucleotide sequence.

At the end of the run, the product is cleaved from the CPG using 25% ammonia solution. The bases of the resultant oligonucleotide are then deprotected by heat-treatment at 55° C. in the presence of ammonia for 5 hours.

The product is evaporated to dryness to remove the ammonia, reconstituted in water and dried again, and finally reconstituted in water. The product is stored at –20° C. until further use.

EXAMPLE 7

Preparation of the Probe

The oligonucleotide HOPE4 (5' CTCTCTTTAA ACAC-CATGCT AACACAGT 3') (SEQ ID NO:6) was synthesized using a DNA synthesizer (Applied Biosystems). It was then chemically coupled to bovine serum albumin, which was immobilized onto the wells of a polystyrene microtiter plate according to the method of Running and Urdea, op. cit., and Nagata, et al., op. cit.

EXAMPLE 8

Evaluation of Samples

Eight seropositive samples were examined, plus a DNA sample prepared from an infected culture of CEM cells. Several seronegative samples were also examined. A positive control-plasmid derived cloned sequences of HIV-I, and a negative control, were always included.

Some samples were analyzed by applying CER and others by ACER. Amplification products were detected by either in solution hybridization with a specific radiolabeled probe (HOPE 3) and subsequent acrylamide gel electrophoresis or the ELISA-like colorimetric assay using as label a biotinylated dNTP analog or a labeled primer (HOPE 2).

The values obtained were as follows:

| Absorbance readings of ELISA-like assay: | | |
|---|---|---|
| 1 POS) | 0.40 | seropositive (5 yrs) |
| 2 POS) | 0.30 | seropositive (1 yr) |
| 3 POS) | 0.60 | dead |
| 4 POS) | 0.20 | seropositive (1.5 yrs) |
| 5 POS) | 0.40 | under AZT (4 yrs) |
| 6 POS) | 0.55 | dead |
| 7 POS) | 0.30 | seropositive (2 yrs) |

-continued

| Absorbance readings of ELISA-like assay: | | |
|---|---|---|
| 8 POS) | 0.20 | seropositive (1 yr) |
| 9 CEM) | 0.60 | infected cell line |
| 10 CONT) | 1.00 | plasmid clone of HIV-I |
| 11 CONT) | 0.06 | yeast DNA |
| 12 CONT) | 0.05 | no DNA |
| 13 NEG) | 0.07 | seronegative |
| 14 NEG) | 0.06 | seronegative |

We claim:

1. A method for amplifying an HIV-1 DNA target nucleic acid sequence in a sample, wherein said target sequence consists of complementary strands having the nucleotide sequence 1317–1379 of pHXB2, comprising the steps of:

(a) adding deoxynucleoside triphosphates, primer pairs comprising two oligonucleotide primers having the nucleotide sequences

5' GAAGGAGCCA CCCCACAAG 3'    (SEQ ID NO: 1)

and

5' GGCTGCTTGA TGTCCCCCC 3',    (SEQ ID NO: 2)

and a nucleic acid polymerase to said sample;

(b) denaturing said target nucleic acid sequence to form separate strands; and (c) maintaining a single reaction temperature selected from within a range from 68° C. to 80° C. and appropriate reaction conditions sufficient to permit specific hybridization and application through the following cycle: said primers hybridize to said strands of said target sequence, primer extension products, which are hybridized to said strands, are formed from said primers and said nucleoside triphosphates, said extension products separate from said strands to become templates for said primers, and new primer extension products are formed, wherein said hybridization, extension, and separation in said cycle occur at the same temperature.

2. A method for detecting or measuring a target nucleic acid sequence in a sample, wherein said target sequence consists of two complementary strands of HIV-1 DNA, comprising the steps of:

(a) amplifying said target sequence according to claim 1, wherein some of said deoxynucleoside triphosphates are biotin-labeled, thereby producing nucleotide sequences that are copies of said target nucleotide sequence and contain one or more biotin-labeled nucleotides;

(b) rendering said nucleotide sequences single-stranded;

(c) contacting said sample containing said single-stranded nucleotide sequences with immobilized probes, each of which comprises a single-stranded polynucleotide attached to a solid support that hybridizes with one of said single-stranded nucleotide sequences, wherein said single-stranded polynucleotide of said probe comprises an oligonucleotide probe having the nucleotide sequence

| 5' TTTAAACACC ATGCTAAACA CAGT 3' | (SEQ ID NO: 3) |
|---|---|
| | or |
| 5' CTCTCTTTAA ACACCATGCT AACACAGT 3' | (SEQ ID NO: 6) | for a sufficient time and under appropriate hybridizing conditions to permit specific hybridization of said polynucleotides with said single-stranded nucleotide sequences, thereby forming bound complexes of said polynucleotides and said single-stranded nucleotide sequences;

(d) washing said bound complexes; and (e) detecting or measuring the presence of biotin in said bound complexes.

3. The method of claim 1 or 2 wherein said target sequence is denatured by heating said sample to 95° C.

4. The method of claim 3 wherein the reaction temperature in step (c) is maintained at 75° C.

5. The method of claim 4 wherein the cycle of step (c) is repeated 10 to 25 times.

6. The method of claim 1 or 2 wherein the reaction temperature and conditions of step (c) are maintained for a time from 1.0 hours to 2.5 hours.

7. The method of claim 2 wherein said solid support is a microtiter plate.

8. The method of claim 2 wherein said detecting or measuring step comprises the steps of:

contacting said bound complexes with a detectable moiety that binds to biotin; and detecting or measuring said detectable moiety.

9. The method of claim 8 wherein said detectable moiety is avidin-horseradish peroxidase.

10. The method of claim 2 wherein said detecting or measuring step comprises the steps of:
   contacting said bound complexes with a first moiety that binds to biotin;
   adding a second moiety comprising biotin bound to a detectable moiety, whereby the biotin in said second moiety binds to said first moiety; and
   detecting or measuring said detectable moiety.

11. The method of claim 10 wherein said first moiety is avidin and said detectable moiety is horseradish peroxidase.

12. A pair of oligonucleotide primers for use in amplifying a target nucleic acid sequence of HIV-1 DNA comprising an oligonucleotide having the nucleotide sequence:

| 5' GAAGGAGCCA CCCCACAAG 3' | (SEQ ID NO: 1) | and an oligonucleotide having the nucleotide sequence:

| 5' GGCTGCTTGA TGTCCCCCC 3' | (SEQ ID NO: 2). |

13. A kit for detecting or measuring the presence of a target nucleic acid sequence in a sample suspected of containing said sequence comprising, in a container:
   (a) biotin-labeled nucleoside triphosphates; and
   (b) a pair of oligonucleotide primers comprising an oligonucleotide having the nucleotide sequence:

| 5' GAAGGAGCCA CCCCACAAG 3' | (SEQ ID NO: 1) | and an oligonucleotide having the nucleotide sequence:

| 5' GGCTGCTTGA TGTCCCCCC 3' | (SEQ ID NO 2). |

14. The kit of claim 13 further comprising a probe that is complementary to and hybridizes with said target sequence.

15. The kit of claim 14 further comprising means for detecting or measuring said biotin.

16. The kit of claim 15 further comprising a nucleic acid polymerase.

17. The kit of claim 14 wherein said probe comprises an oligonucleotide probe having the nucleotide sequence

| 5'TTTAAACACC ATGCTAAACA CAGT3' | (SEQ ID NO: 3). |

18. A kit for detecting or measuring the presence of a target nucleic acid sequence in HIV-1 DNA in a sample suspected of containing said sequence comprising, in a container:
   (a) biotin-labeled nucleoside triphosphates;
   (b) a pair of oligonucleotide primers having the nucleotide sequences

| 5' GAAGGAGCCA CCCCACAAG 3' | (SEQ ID NO: 1) |
| and | |
| 5' GGCTGCTTGA TGTCCCCCC 3' | (SEQ ID NO: 2) | and
   (c) an oligonucleotide probe having the nucleotide sequence

| 5' TTTAAACACC ATGCTAAACA CAGT 3' | (SEQ ID NO: 3). |

* * * * *